(12) United States Patent
Brittner

(10) Patent No.: US 9,636,282 B2
(45) Date of Patent: May 2, 2017

(54) HANDS FREE BREAST PUMP

(71) Applicant: Lyndon Brittner, Provo, UT (US)

(72) Inventor: Lyndon Brittner, Provo, UT (US)

(73) Assignee: Oak Tree IP, LLC, Orem, UT (US)

( * ) Notice: Subject to any disclaimer, the term of this patent is extended or adjusted under 35 U.S.C. 154(b) by 0 days.

(21) Appl. No.: 14/613,240

(22) Filed: Feb. 3, 2015

(65) Prior Publication Data

US 2015/0196460 A1 Jul. 16, 2015

Related U.S. Application Data

(63) Continuation of application No. 12/898,600, filed on Oct. 5, 2010, now Pat. No. 8,945,046, which is a
(Continued)

(51) Int. Cl.
*A61J 13/00* (2006.01)
*A61M 1/06* (2006.01)
(Continued)

(52) U.S. Cl.
CPC .................. *A61J 13/00* (2013.01); *A61J 9/00* (2013.01); *A61M 1/06* (2013.01); *A61M 1/064* (2014.02);
(Continued)

(58) Field of Classification Search
CPC ............ A61M 25/10; A61M 2025/105; A61M 25/1002; A61M 25/104; A61M 25/1011;
(Continued)

(56) References Cited

U.S. PATENT DOCUMENTS

| 949,414 A | 2/1910 | Cunningham |
| 1,259,309 A | 3/1918 | Somers |

(Continued)

FOREIGN PATENT DOCUMENTS

| CN | 2922916 | 1/2006 |
| GB | 2366732 | 3/2002 |

(Continued)

OTHER PUBLICATIONS

International Search Report and Written Opinion of the International Searching Authority for PCT Application No. US2009/039335, Jul. 27, 2009.
(Continued)

*Primary Examiner* — Scott Medway
(74) *Attorney, Agent, or Firm* — Durham Jones & Pinegar; Christopher L. Wight; Randall B. Bateman

(57) ABSTRACT

A hands-free breast pump system is disclosed. A breast shield having an adhesive inner surface for adhering to a woman's breast is disclosed. The breast shield may be connected to an adapter for transferring a vacuum generated by a pump to the breast. The adapter also allows milk expressed from the breast to drain from the adapter to a container. In the alternative, the breast shield may form part of a breast shield adapter system which is connected to a conventional breast shield by a drain line so that a conventional breast pump system is used to supply a vacuum and to collect the milk.

2 Claims, 15 Drawing Sheets

Related U.S. Application Data continuation-in-part of application No. 12/417,423, filed on Apr. 2, 2009, now abandoned.

(60) Provisional application No. 61/042,095, filed on Apr. 3, 2008.

(51) Int. Cl.
  *A61J 9/00* (2006.01)
  *A61M 39/10* (2006.01)
  *A61M 39/20* (2006.01)

(52) U.S. Cl.
  CPC ............ *A61M 1/066* (2014.02); *A61M 39/10* (2013.01); *A61M 39/20* (2013.01); *A61M 2205/0216* (2013.01); *A61M 2210/1007* (2013.01)

(58) Field of Classification Search
  CPC .. A61M 2025/1052; A61M 2025/1086; A61M 2025/1084; A61M 2025/1088; A61M 25/0017; A61M 29/02; A61M 2025/1004; A61M 25/005; A61M 25/04
  USPC .................................................. 604/73, 74
  See application file for complete search history.

(56) References Cited

U.S. PATENT DOCUMENTS

| | | | |
|---|---|---|---|
| 2,364,866 A | 12/1944 | Meynier | |
| 2,516,354 A * | 7/1950 | Taylor | 119/14.41 |
| 3,382,867 A | 5/1968 | Reaves | |
| 3,782,378 A | 1/1974 | Page | |
| 3,977,405 A | 8/1976 | Yanase | |
| 4,084,589 A * | 4/1978 | Kulvi | 604/73 |
| D251,015 S | 2/1979 | Cone | |
| 4,323,067 A | 4/1982 | Adams | |
| 4,607,596 A | 8/1986 | Whittlestone et al. | |
| D288,004 S | 1/1987 | Blachly | |
| 4,680,028 A | 7/1987 | Stuart | |
| 4,813,932 A | 3/1989 | Hobbs | |
| 4,857,051 A | 8/1989 | Larsson | |
| 4,929,229 A | 5/1990 | Larsson | |
| 4,964,851 A | 10/1990 | Larsson | |
| 4,992,074 A | 2/1991 | Diaz | |
| 5,049,126 A | 9/1991 | Larsson | |
| 5,071,403 A | 12/1991 | Larsson | |
| 5,100,406 A * | 3/1992 | Panchula | 604/74 |
| 5,178,095 A | 1/1993 | Mein | |
| 5,358,476 A | 10/1994 | Wilson | |
| 5,514,166 A * | 5/1996 | Silver et al. | 604/74 |
| 5,542,921 A | 8/1996 | Meyers et al. | |
| 5,586,518 A | 12/1996 | Carrano | |
| 5,616,125 A | 4/1997 | Jelks | |
| 5,645,081 A * | 7/1997 | Argenta et al. | 128/897 |
| 5,720,722 A | 2/1998 | Lockridge | |
| 5,797,875 A | 8/1998 | Silver | |
| 5,897,580 A | 4/1999 | Silver | |
| 6,139,521 A | 10/2000 | Larsson | |
| 6,200,195 B1 | 3/2001 | Furuno et al. | |
| 6,210,360 B1 | 4/2001 | Kong | |
| 6,358,226 B1 | 3/2002 | Ryan | |
| 6,379,327 B2 | 4/2002 | Lundy | |
| 6,440,100 B1 * | 8/2002 | Prentiss | 604/74 |
| 6,673,036 B1 | 1/2004 | Britto | |
| 6,676,610 B2 | 1/2004 | Morton et al. | |
| 6,676,631 B1 | 1/2004 | Greter | |
| 6,685,675 B1 * | 2/2004 | Hadvary et al. | 604/180 |
| 6,723,066 B2 | 4/2004 | Larsson | |
| 6,758,720 B2 | 7/2004 | Chen | |
| 6,780,081 B2 | 8/2004 | Chen et al. | |
| 6,866,994 B2 * | 3/2005 | Morton | 435/4 |
| 6,899,696 B2 | 5/2005 | Morton et al. | |
| 6,974,440 B2 | 12/2005 | Silver | |
| 6,988,930 B2 | 1/2006 | Gillan | |
| 7,001,241 B2 | 2/2006 | Gorringe et al. | |
| 7,029,462 B2 | 4/2006 | Hung et al. | |
| 7,204,829 B2 | 4/2007 | Hung et al. | |
| 7,223,255 B2 | 5/2007 | Myers et al. | |
| 7,278,899 B2 | 10/2007 | Davis | |
| 7,648,467 B2 * | 1/2010 | Wang et al. | 600/573 |
| 8,075,516 B2 * | 12/2011 | Pfenniger et al. | 604/73 |
| 9,033,953 B2 * | 5/2015 | Felber | 604/514 |
| 2001/0031911 A1 | 10/2001 | Khouri | |
| 2001/0038799 A1 | 11/2001 | Silver | |
| 2002/0062103 A1 | 5/2002 | Larsson | |
| 2003/0004459 A1 * | 1/2003 | McKendry et al. | 604/74 |
| 2003/0073951 A1 * | 4/2003 | Morton et al. | 604/73 |
| 2003/0135181 A1 | 7/2003 | Chen et al. | |
| 2003/0139702 A1 * | 7/2003 | Renz et al. | 604/74 |
| 2003/0191427 A1 | 10/2003 | Jay et al. | |
| 2004/0087917 A1 | 5/2004 | Barakat et al. | |
| 2004/0122358 A1 | 6/2004 | Kent et al. | |
| 2005/0043677 A1 | 2/2005 | Kelly et al. | |
| 2005/0154349 A1 | 7/2005 | Renz et al. | |
| 2005/0234370 A1 | 10/2005 | Beal et al. | |
| 2005/0283112 A1 | 12/2005 | Britto | |
| 2006/0106334 A1 | 5/2006 | Jordan et al. | |
| 2006/0111665 A1 | 5/2006 | Gillan | |
| 2006/0116632 A1 | 6/2006 | Gillan | |
| 2006/0270973 A1 | 11/2006 | Chu | |
| 2007/0060855 A1 | 3/2007 | Leung et al. | |
| 2007/0219486 A1 | 9/2007 | Myers et al. | |
| 2008/0045888 A1 | 2/2008 | Edwards et al. | |
| 2008/0090444 A1 | 4/2008 | Luzbetak et al. | |
| 2008/0125703 A1 | 5/2008 | Ihm | |
| 2008/0208116 A1 | 8/2008 | Dao et al. | |
| 2008/0287037 A1 * | 11/2008 | Solberg | 450/36 |
| 2009/0254028 A1 | 10/2009 | Brittner | |
| 2009/0298386 A1 * | 12/2009 | Deal et al. | 450/81 |
| 2010/0152652 A1 | 6/2010 | Weston | |
| 2011/0251552 A1 | 10/2011 | Brittner | |
| 2012/0136325 A1 * | 5/2012 | Allen et al. | 604/319 |
| 2012/0150123 A1 * | 6/2012 | Lawrence et al. | 604/180 |
| 2012/0165730 A1 * | 6/2012 | McCoy | 604/76 |
| 2014/0012119 A1 * | 1/2014 | Geaghan et al. | 600/365 |
| 2015/0051560 A1 * | 2/2015 | Askem | 604/319 |

FOREIGN PATENT DOCUMENTS

| | | |
|---|---|---|
| JP | 63-146650 | 9/1988 |
| JP | H10-512477 | 7/1996 |
| JP | H11-323616 | 11/1999 |
| JP | H2000-054202 | 2/2000 |
| JP | 2004-201686 | 7/2004 |
| JP | 2007-089904 | 4/2007 |
| KR | 0113723 A | 11/2007 |
| WO | WO 03105616 | 12/2003 |

OTHER PUBLICATIONS

International Search Report and Written Opinion of the International Searching Authority for PCT Application No. US2011/054649, Apr. 20, 2012.
Simply Lily, website showing product "Lilypadz" which applicant believes was available prior to filed of present application, <http://www.simplylily.com/product1.html>.
"Adhere—Definition." Miriam-Webster Dictionary. Retrieved Dec. 27, 2010. Online: <http://www.merriamwebster.com/disctionary/adhere>.
Rule 1.132 Declaration of C. Todd Kinard, Dec. 6, 2011.
Patent Examination Report No. 1 from IP Australia for Australian Patent Application No. 2009231652, Jul. 25, 2013.
Patent Examination Report No. 1 from Australian Patent Application No. 2011312325, Feb. 17, 2014.
Office Action from RU Patent Application No. 2010140209/14(057605), Feb. 6, 2013.
Office Action from Malaysian Patent Application No. PI 2010004616, Sep. 13, 2013.
Office Action from Israel Patent App. 208414, Sep. 22, 2011.
English Translation of Office Action from Japanese Patent Appln. No. 2011-503181, Jul. 9, 2013.

(56) References Cited

OTHER PUBLICATIONS

English Translation of Final Office Action from Japanese Patent Appln. No. 2011-503181, Jan. 3, 2014.
Office Action from Chinese Patent App. No. 200980117871.9, Dec. 5, 2012.
Office Action from Chinese Applicant No. 200980117871.9, Aug. 20, 2013.
Office Action from Chinese Applicant No. 200980117871.9, May 15, 2014.
Search Report from Intellectual Property Office of Singapore from Singapore Application No. 201302305-6, Jun. 10, 2014.

\* cited by examiner

HANDS FREE BREAST PUMP

PRIORITY

This application is a continuation-in-part of U.S. patent application Ser. No. 12/417,423, filed Apr. 2, 2009, which is incorporated herein by reference in its entirety, and claims priority to U.S. Provisional Patent Application No. 61/042,095, filed on Apr. 3, 2008, which is incorporated herein by reference in its entirety.

FIELD OF THE INVENTION

The present invention relates to breast-milk collection systems. More specifically, the present invention relates to hands-free breast pump systems and hands-free breast shield adapters.

BACKGROUND

Studies show that mother's breast milk is more healthy for infants than formula or other types of milk. While mothers strive to provide the best environment for their children, sometimes this requires that the mother cannot be with a nursing infant at all times. For example, some women work outside the home some amount of time during the day. A nursing mother who works outside the home must collect milk during the day to provide breast milk for her child when she is away from her child. If a nursing mother does not utilize a breast pump, her milk production can wane, such that she is not able to produce enough milk for her infant. Thus, many working mothers collect breast milk to be able to work and provide the best nourishment for their infants. To accommodate nursing mothers, breast pumps for expressing breast milk for later use by their infants have been around for some time.

Typically, these breast pumps include a funnel, or parabolic-shaped cup, similar to a suction cup (sometimes referred to as a breast shield), which is placed over the nipple and a portion of the breast. The cup is generally connected to a container for holding the expressed milk and a vacuum pump of some type. Some pumps may be hand-activated, while others are electrically operated. Some are even battery powered.

A vacuum from the pump is generally intermittently generated within the shield to generate negative pressure on the nipple, causing milk to be expressed from the breast within the breast shield. The intermittent nature of the vacuum may be done to simulate a baby sucking at the breast for milk. The expressed milk then generally flows from the shield to a storage container for later use. Most breast pumps require that the woman use her hands to operate the pump and/or maintain connection with the cup and her breast. Such breast pumps have been time consuming and somewhat awkward to use because the woman using the pump must occupy one or both hands, making it difficult to perform other activities.

A variety of breast pumps have been developed that are intended to allow a woman's hands to be free during use of the breast pump. Often, these breast pumps utilize straps, or bra-type structures for holding the shield in place during milk expression. However, these straps and other structures generally provide for additional bulk in the breast pump and are difficult and time consuming to attach, which is not conducive to pumping in locations other than home where the pump may be stored. Some women desire to be out of the house during times when she would need to pump breast milk to maintain milk production. Other pumps require special bras or other clothing, requiring often uncomfortable choices in clothing. Similarly, many breast pumps on the market are uncomfortable, and difficult to use. Thus, a need exists for a simple, comfortable, hands-free breast pump system which enables a woman to do other things while pumping breast milk.

BRIEF SUMMARY

Embodiments of hands-free breast pump systems, methods, adapters and components are described. Some embodiments of breast pump systems may include a formed member, or breast shield, made of a material that provides for an adhesive inner surface for adhering to a woman's breast. The adhesiveness of the surface may be due to the materials used during manufacturing (i.e. a breast shield which is made from an adhesive material or has an adhesive added or applied during the manufacturing processes) and not due to adhesive sprays, lotions, or other items placed on the breast shield or the breast by the end-user. In the alternative, adhesive could be added to the breast shield either to make it adhesive or to renew the adhesive qualities of the breast shield lost during use and washing by the end user. Such could be provided, for example, in a kit which allows the user to renew the adhesive qualities when they are lost.

In some embodiments, breast pump systems may include a breast shield adapter or coupling connected to the breast shield for transferring a vacuum generated by a pump to the breast to express milk. The breast shield adapter also allows milk expressed from the breast to drain from the adapter to a container, without travelling into the pump. In some embodiments, the breast shield adheres to the breast due to the adhesive and supports the weight of the adapter, breast shield, and tubing extending from the adapter without the need for separate adhesives, gels, straps, or specially designed support bras. In other embodiments, the adhesive qualities of the breast shield may be enhanced by the user applying adhesive to the breast shield. Thus, the adhesive breast shield and breast pump system may allow for hands-free expression of milk.

In some embodiments, a breast pump system comprises a breast shield for adhesive attachment to the breast, one or more tubes for conveying vacuum pressure and milk and a connector for plugging into the breast shield or adapter of a conventional breast pump system. In such an embodiment, a conventional pump system can be used when desired, and the hands-free components quickly added without altering the conventional pump system when hands-free pumping is desired.

Figure 1:
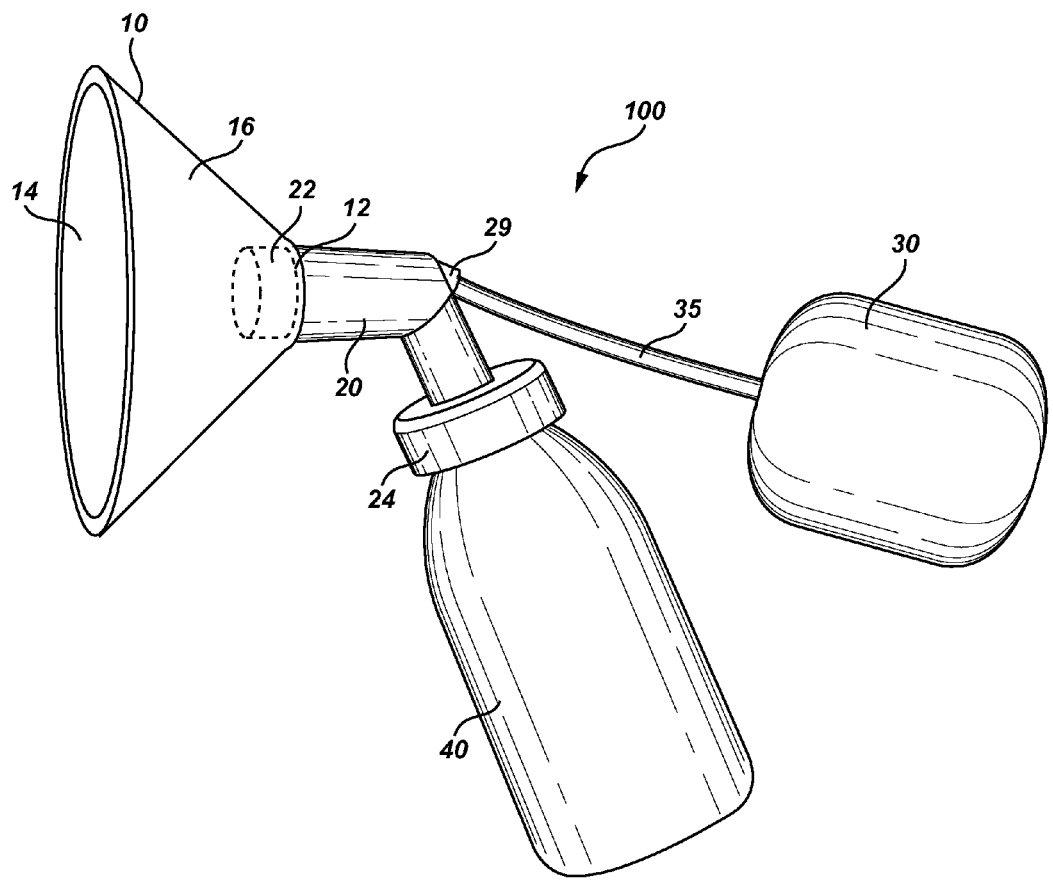
FIG. 1 illustrates a generalized perspective view of an exemplary embodiment of a breast pump system.

Together with the following description, the Figures demonstrate and explain the principles of a hands free breast pump system and associated components and methods. In the Figures, the thickness and configuration of components may be exaggerated for clarity. The same reference numerals in different Figures represent the same component.

DETAILED DESCRIPTION

Embodiments of a hands-free breast pump system are described below and shown in the Figures. Breast pump system 100, as shown in FIG. 1, includes a breast shield 10, an adapter 20, pump 30, vacuum line 35, vacuum line connector 29, container connector 24, and container 40.

The breast shield 10 will typically have an outer surface 16 and an inner surface 14. The breast shield 10 may be made of a relatively soft, flexible material capable of conforming to a woman's breast. Not only is the soft, flexible material more comfortable, it can also help to adhere the breast shield to the breast as the breast shield can be rolled outwardly, placed against the breast and then released so that the inner surface conforms to the woman's breast.

Inner surface 14 is preferably adhesive in nature so that breast shield 10 will adhere to a woman's breast without the need for external support structures (although such structures could be used if desired). This may be due to the inner surface being made from a naturally adhesive material, or due to adhesive applied to the inner surface of the breast shield. It will be appreciated that adhesive may also be provided to renew the adhesive nature of the inner surface which may be lost due to use and washing of the breast shield. Thus, the breast shield 10 may be sold as part of a kit which includes adhesive to allow the user to apply additional adhesive to the breast shield to ensure that the adhesive is strong enough to support the weight of the breast pump system 100 and milk contained in the container 40.

Because of the adhesive nature of inner surface 14 of the breast shield 10, inner surface 14 may attract dirt, lint, skin cells, oil, and other materials that may reduce the adhesiveness of inner surface 14. In that situation, inner surface 14 may be washed with soap and water, boiled, or otherwise cleaned to restore the adhesiveness of inner surface 14. Over time, breast shield 10 may become worn, lose some adhesion properties, or otherwise require replacement. In such cases, the breast shield 10 may be removed from adapter 20 and replaced as necessary. Additionally, a cleanser may be provided as part of a kit to allow cleaning of the adhesive inner surface 14 with minimal impact on the adhesive.

The adhesive nature of inner surface 14 of the breast shield 10 preferably allows breast shield 10 to remain affixed to a woman's breast during the duration required to express a required or desired amount of milk or until dry. Preferably, though not required, the adhesive portion may cover most, if not all, of the inner surface 14 to maximize the area of the breast shield which is available to support the weight of the breast pump system 100 and the milk in the container 40. This allows the breast shield 10 to be used in a hands-free manner. This may be done without the need for separate consumer applied adhesives, gels, straps, or specialty bras designed for holding a breast pump system in place, (although additional adhesive may be added as needed). Similarly, it allows use of breast pump system 100 without requiring the woman to hold breast shield 10 in place with her hands. Therefore, a woman using the breast shield 10 with pump system 100 may be able to express milk and still have use of her hands free for other activities. Thus, for example, a woman at work could close her office door, attach the breast pump system and then express milk while continuing to type, talk on the telephone or do a number of other activities which require use of the hands. Additionally, the breast shield 10 may be more comfortable than previously known breast shields because it conforms to the breast.

It will be appreciated that pump 30 may be a manual pump in which case the woman may use one hand to drive the pump while leaving the other hand free for other tasks. In the alternative, pump 30 may be a powered pump running on A/C current or batteries thereby leaving both hands of the woman free during the pumping process. Either way, the adhesive nature of the breast shield allows the woman to perform tasks which would not be feasible if she were required to use one hand to hold the breast shield to the breast during use. Additionally, the present invention obviates the requirement for specialty bras and the like configured to hold a conventional breast shield.

The breast shield 10 may be made from any appropriate material that imparts the desired attributes of flexibility and adhesiveness to skin. In certain embodiments, breast shield 10 may be made from an elastomeric material that has been sufficiently plasticized along inner surface 14 to provide the desired material characteristics. For example, the breast shield 10 may be made from a silicone rubber with suitable plasticizers. In other examples, the breast shield 10 may be made from Styrene-Ethylene-Butylene-Styrene (SEBS), Styrene-Ethylene-Propylene-Styrene (SEPS), and Styrene-Ethylene-Ethylene-Propylene-Styrene (SEEPS) copolymers. Other materials may also be appropriate. For example, suitable plasticizers for elastomers may include oils such as mineral oils, resins, rosins, and others. Other components may be used with the elastomers as well, such as antioxidants, colorants, bleed reducing additives, etc. Furthermore, fragrances, such as a baby powder or other calming sent may also be included.

In some embodiments, a coating may be applied during manufacture to provide the necessary adhesive properties. Depending on the desired structure, rigidity, softness, etc., any suitable process or materials may be used to construct the breast shield 10, as desired. For example, in some instances it may be desirable to have more or less rigidity than others.

The material used in forming the breast shield 10 may be manufactured by solvent blending, melt blending, or compounding under heat and pressure such as by use of a single screw or twin screw compounding machine or otherwise. Breast shield 10 may be constructed by injection molding, casting, or another desired process.

The breast shield 10 may be configured in any shape and dimension compatible with a woman's breast, as desired. For example, some embodiments of breast shield 10 may be funnel-shaped or cup-shaped. It should be understood that breast shield 10 may be produced and marketed in a number of sizes and shapes in order to be compatible with a wide range of breast dimensions, profiles, and shapes. The breast shield 10 may include opening 12 for connecting the breast shield 10 to the connector sleeve 22 of the adapter 20. The breast shield 10 may also be manufactured to work with known breast pump systems in place of the conventional breast shield.

In some embodiments, the breast shield 10 may be able to invert, such that inner surface 14 is temporarily on the outside and outer surface 16 is temporarily on the inside. By inverting the breast shield 10 a woman using breast pump system 100 may be able to achieve a tighter, more secure fit. A woman may first place an opening of the adapter 20 over the nipple in a desired position, and then extending or rolling the breast shield 10 over the breast as the breast shield is returned to the normal state, ensuring maximum contact, fit, and adhesive contact between the breast shield 10 and the breast. With the breast shield attached to the breast, the adhesive inner surface 14 engages the breast and is able to support the weight of the breast pump system 100 and collected milk.

Turning now to adapter 20, embodiments of the adapter 20 may provide for introducing a vacuum to the woman's breast and for directing the flow of milk to a container 40. The adapter 20 may include a connector for connecting to the breast shield 10. For example, the adapter 20 may include a connector sleeve 22 that forms an interference connection with the opening 12 and inner surface 14 of the breast shield 10. The opening 12 may be stretched around the sleeve 22 to form an interference fit. The end of the sleeve 22 may be configured to seal against or around the areola of a breast. The sleeve 22 may also be configured so that the nipple of the breast extends inside the sleeve 22. Thus, the adapter 20 may come in different sizes to accommodate breasts having different nipple sizes. The inner surface 14 may be configured to adhere to the skin of the breast surrounding the areola. It will be appreciated, that it may be desirable for the inner surface not to seal over the areola so that the breast shield does not interfere with the pumping action of the breast pump system.

In some embodiments, the sleeve 22 may be generally flush with the opening 12 in the breast shield 10. For example, the sleeve 22 may include a groove or lip on or near the edge extending into the breast shield 10 for holding the inside of the opening 12. Similarly, the opening 12 of the breast shield 10 may include a complimentary structure to allow coupling of the sleeve 22 and breast shield 10. In other embodiments, the adapter 20 and the breast shield 10 may be a unitary structure.

The adapter 20 may include a connector 24 for connecting adapter 20 to the container 40. For example, the connector 24 may be threaded to engage threads on the container 40. The adapter 20 may be configured such that milk drawn into the adapter 20 drains into the container 40, without going into the pump 30. The container 40 may be any container used for receiving expressed milk or a modification thereof. For example, the container 40 may be a standard baby bottle, or other container commonly used to store and/or deliver milk to an infant The adapter 20 may be connected through a vacuum line connector 29 to the pump 30 via a vacuum line 35. Negative pressure generated by the pump 30 may be transmitted to the adapter 20 via the vacuum line 35 and thereby to the interior of the breast shield 10 and sleeve 22. The pump 30 may be any pump or device suitable for delivering vacuum pressure sufficient for expressing milk. Vacuum line 35 may be made of any material capable of transferring negative pressure from the pump 30 to the adapter 20, and may be any desired configuration. For example, the vacuum line 35 may be plastic tubing, such as Polyvinyl Chloride (PVC) tubing.

The vacuum line 35 may be connected to the pump 30 and vacuum line connector 29 of the adapter 20 via any type of connector desired. For example, the vacuum line connector 29 may include an opening about the same diameter or slightly smaller than the outer diameter of the vacuum line 35, providing for a press or interference fit of the outside of the vacuum line into the adapter 20. Similarly, the vacuum line connector 29 may include an inner flange for an appropriate fit with the inner surface of the vacuum line 35. Similarly, the vacuum line connector 29 may be oriented in any desired direction from the adapter 20, depending on the desired location of the pump 30. For example, the vacuum line connector 29 may be oriented such that the vacuum line 35 extends collinearly with a drain line 45 to minimize the profile of adapter 20 when attached to a breast. Thus, for example, a woman could position the system beneath her shirt with minimal disruption to its normal appearance.

In some embodiments, the adapter 20 may be specially designed to meet the functional requirements described herein. In any of the embodiments, it may be desirable to have the adapter 20 be as small as possible to reduce the weight of adapter 20. Similarly, the adapter 20 may be made of light materials to reduce the weight being born by breast shield 10, and the woman's breast. The adapter 20 may also be manufactured to be compatible with any desired commercially available pump.

Figure 2:
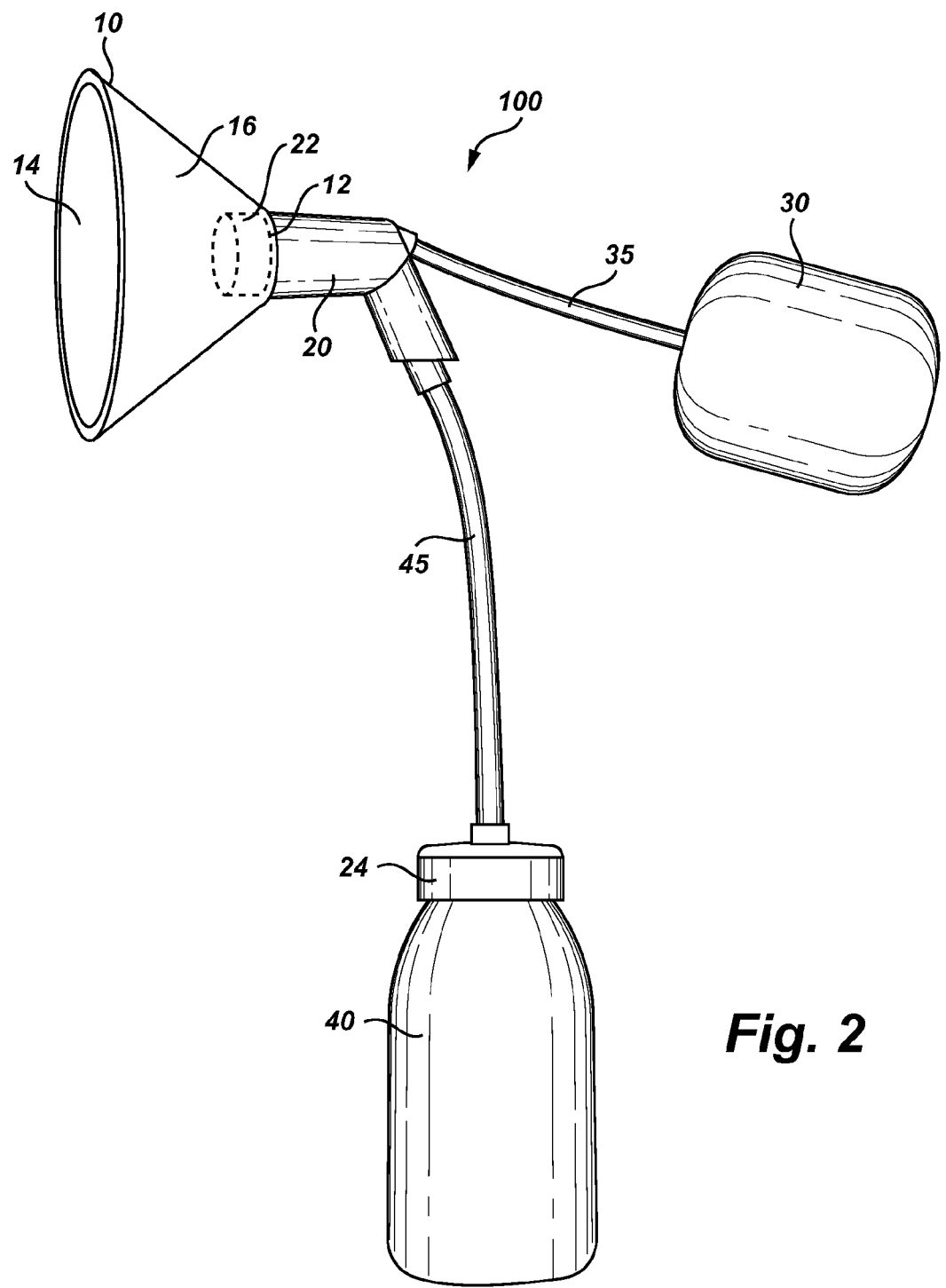
FIG. 2 illustrates a generalized perspective view of an exemplary embodiment of a breast pump system.

FIG. 2 illustrates other embodiments of breast pump system 100 similar to embodiments shown in FIG. 1. In FIG. 2, the container 40 is coupled to the adapter 20 via a drain line 45. The drain line 45 may be coupled to the adapter 20 and the container connector 24. The container connector 24 may contain a valve that closes when negative pressure is generated by the pump 30, creating a vacuum. This valve would open when the pump cycles off the negative pressure, allowing milk to drain into the container 40. Similarly, such a valve may be located on the adapter 20, or as an in-line valve in drain line 45.

Drain line 45 may be long enough that the container 40 may be supported by something other than the adapter 20 and breast shield 10. Depending on the desired use, the drain line 45 may be 6 inches, 10-12 inches or even longer. For example, the container 40 may rest on a table or chair while a woman is expressing milk, or may be held on a belt or other supporting structure. A longer drain line allows the woman more mobility without having to drag the bottle around. Thus, for example, a drain line of 24 inches may allow a woman to comfortably move around her desk while expressing milk and without moving the container 40.

Figure 5:
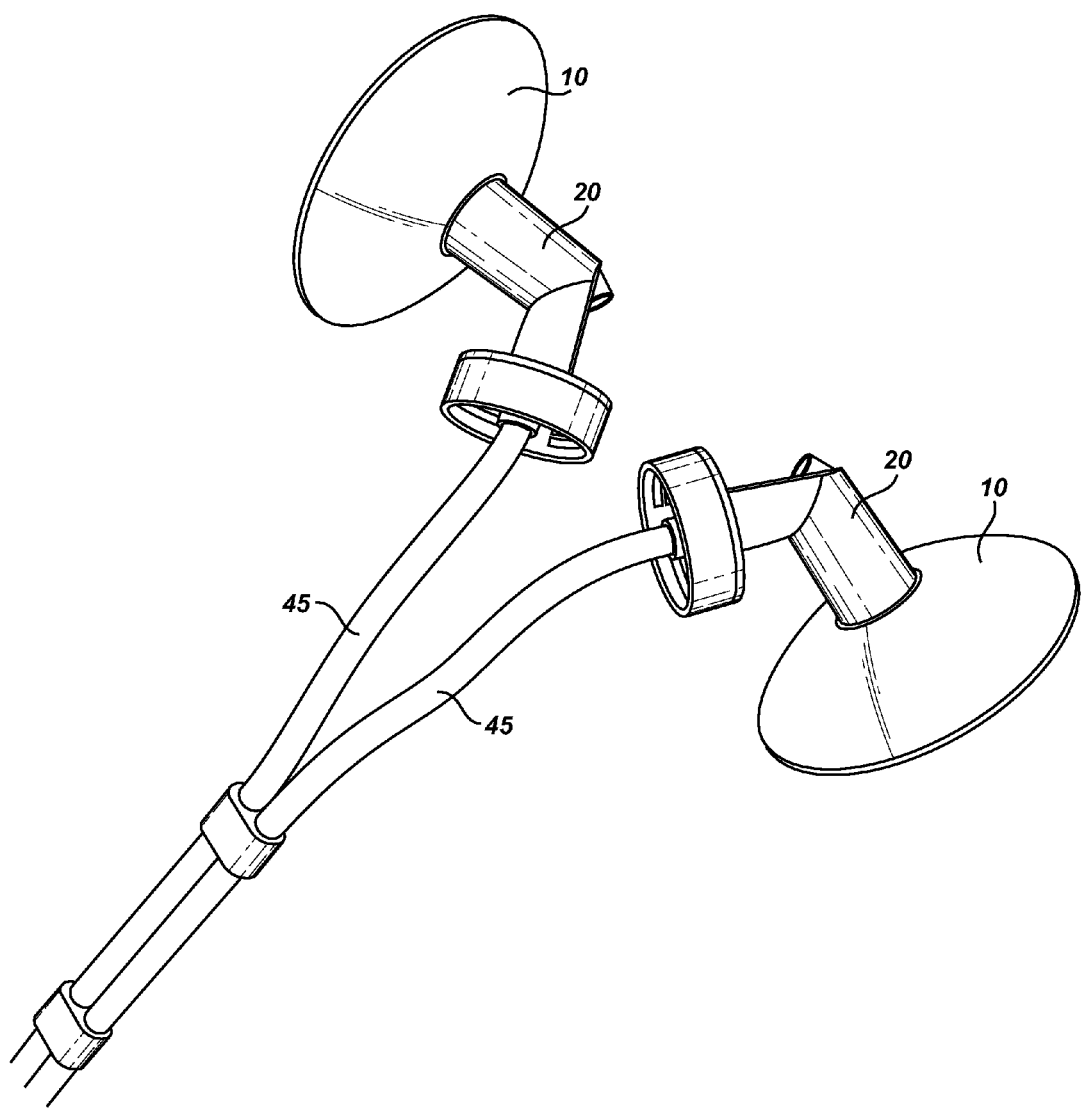
FIG. 5 illustrates a partial assembly of an exemplary breast pump system

Drain line 45 may be any device capable of transferring milk from the adapter 20 to the container 40. For example, the drain line 45 may be plastic tubing, such as PVC tubing, silicone or other food grade material. The drain line 45 may be connected to the adapter 20 and the container 40 via any type of connection means desired. In some embodiments, such as is shown in FIG. 5, adapter 20 may be able to connect directly to the container 40, or to the drain line 45, as desired. Thus, a woman is able to adjust the system 100 for her particular needs at the moment.

Reducing the weight that must be supported by the adapter 20 reduces the weight that must be supported by the adhesive connection of breast shield 10 to a woman's breast, and consequently, by the woman's breast. Therefore, the embodiment of FIG. 2 reduces the adhesive required in the embodiments of FIG. 1 for breast shield 10 to stay adhesively connected to a woman's breast in a hands-free manner.

Figure 3:
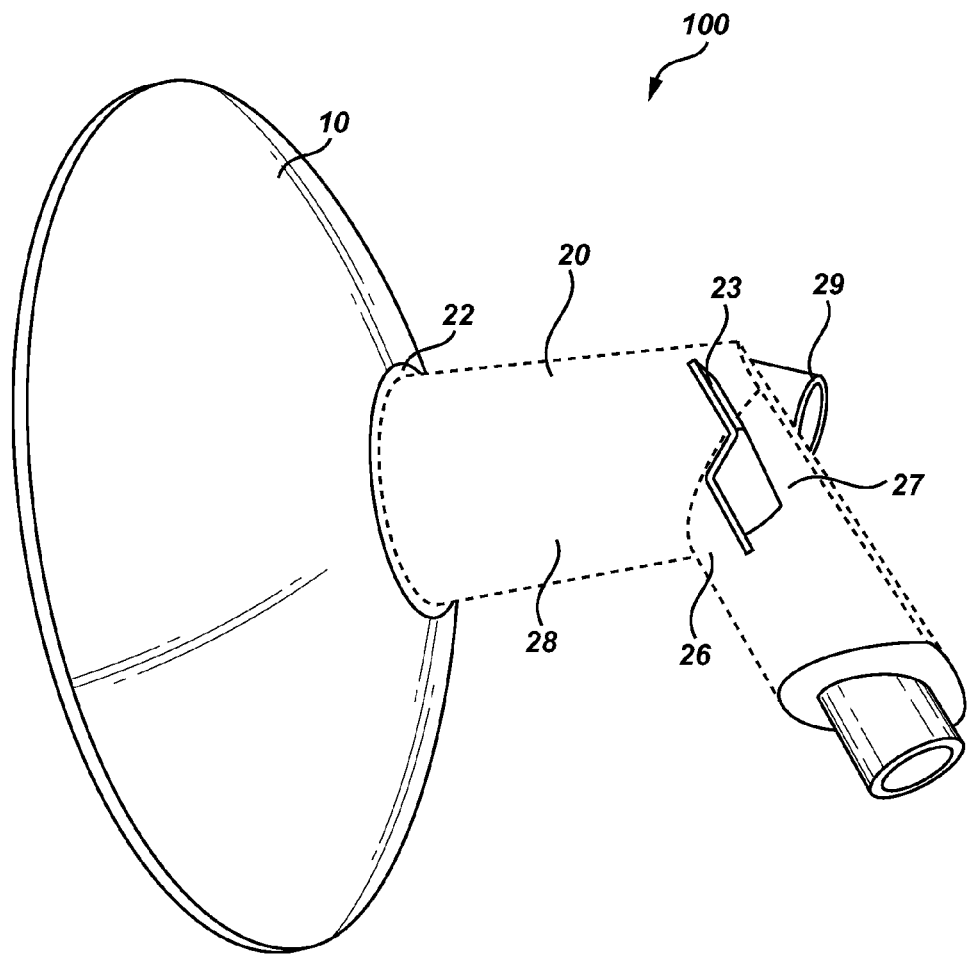
FIG. 3 illustrates a partial assembly of an exemplary breast pump system.

FIG. 3 illustrates the interior of an embodiment of the adapter 20. The adapter 20 may include an interior passageway 28 divided into a liquid passageway 26 and a vacuum passageway 27 by a diverter 23. The diverter 23 may be positioned to prevent expressed milk from being sucked into the pump 30. When in use, milk will be expressed into passageway 28. The diverter 23 channels the milk down liquid passageway 26, and further down by gravity into the container 40. The vacuum line connector 29 is attached to the pump 30, which supplies the negative pressure to express the milk.

Figure 4:
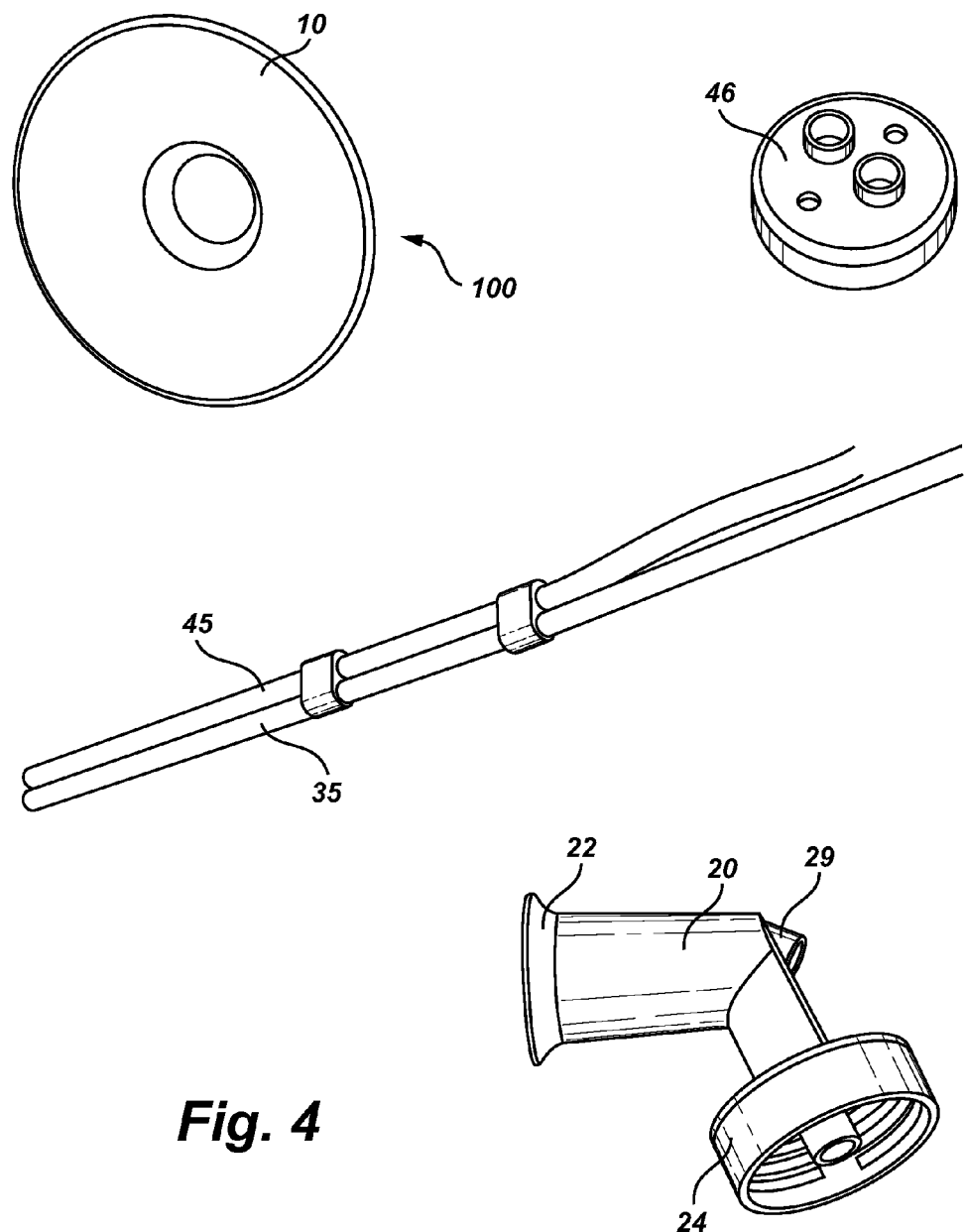
FIG. 4 illustrates components of a partial assembly of an exemplary breast pump system.

FIG. 4 illustrates components of unassembled breast pump system 100 as may be provided to an end user. The system 100 may include the breast shield 10, adapter 20, line connector 46, vacuum line 35, and drain line 45. Line connector 46 may be placed in the opening of a fluid storage container, such as container 40. Line connector 46 may be coupled to both vacuum line 35 and drain line 45, with vacuum line 35 going to a pump, such as pump 30, and drain line 45 going to adapter 20. In some embodiments, vacuum line connector 29 may be capped, as the vacuum is drawn through container 40 and drain line 45, instead of directly through adapter 20. Similarly, in some embodiments, both lines 35 and 45 may function as drain lines 45 running from dual adapters 10 to the same container 40 through line connector 46.

FIG. 5 illustrates twin drain lines 45 connected to twin adapters 20 and breast shields 10 that may be used to express milk from both breasts simultaneously. A single pump or multiple pumps may be coupled to adapters 20 as required. Similarly, each of drain lines 45 may be connected to the same or a different container 40, and may be connected together with a "Y" connector to drain into a single bottle through a single drain line 45. Similarly, a single vacuum line from a single pump may be split with a "Y" connector to attach to both adapters 20. It will be understood that lines 35 and 45 may be connected in any manner to their respective devices and locations, similar to as discussed with respect to vacuum line connector 29 above.

Figure 6:
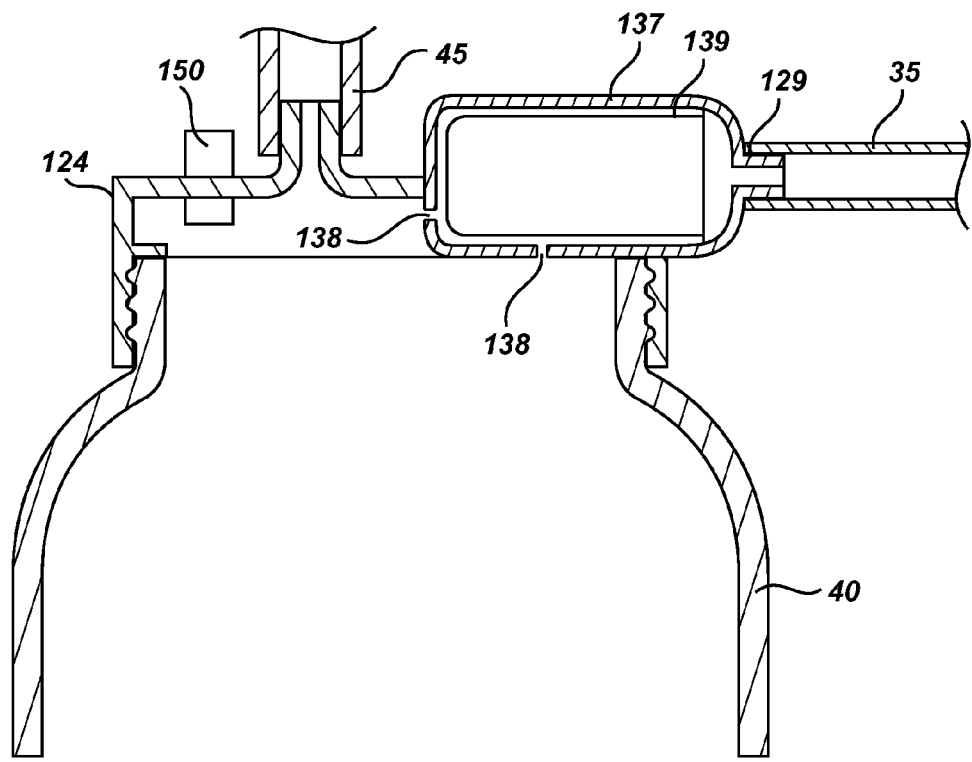
FIG. 6 illustrates a cross-sectional view of a lid assembly of an exemplary breast pump system.

FIG. 6 illustrates a portion of an exemplary breast pump system with container connector 124. Container connector 124 may include valve 137 connected to vacuum line 35 through vacuum line connector 129. Container connector 124 may be coupled to fluid container 40 and drain line 45 similar to embodiments of connector 24 discussed above. However, container connector 124 may allow drain line 45 to both carry the expressed milk to fluid container 40, and to carry the vacuum pressure from vacuum line 35, making it possible to have only one connection to adapter 20, as previously described.

Valve 137 may include collapsible bladder 139, which may collapse as a vacuum is drawn from vacuum line 35, thus producing a pressure drop in fluid container 40, drain line 45 and adapter 20 sufficient to cause milk from a lactating woman's breast to be expressed. The expressed milk may then be drawn down drain line 45 into fluid container 40. Valve 137 may also include air passageways 138 in communication with the interior of fluid container 40.

Container connector 124 may be connected to fluid container 40 with a threaded connection, similar to the connection of connector 24 to fluid container 40 described above. Burp valve 150 may provide for the expulsion of excess pressure from fluid container 40 as milk collects in container 40 to allow valve 137 to continue to provide negative pressure to fluid container 40 and drain line 45.

In some embodiments, valve 137 may be an in-line valve placed in vacuum line 35, and may be constructed in any manner that allows a vacuum to be drawn in drain line 45 while eliminating the possibility of fluid from travelling from fluid container 40 through vacuum line 35 and into pump 30. In some embodiments, valve 137 may not be needed, depending on the configuration of the various parts and components of the breast pump system.

Figure 7:
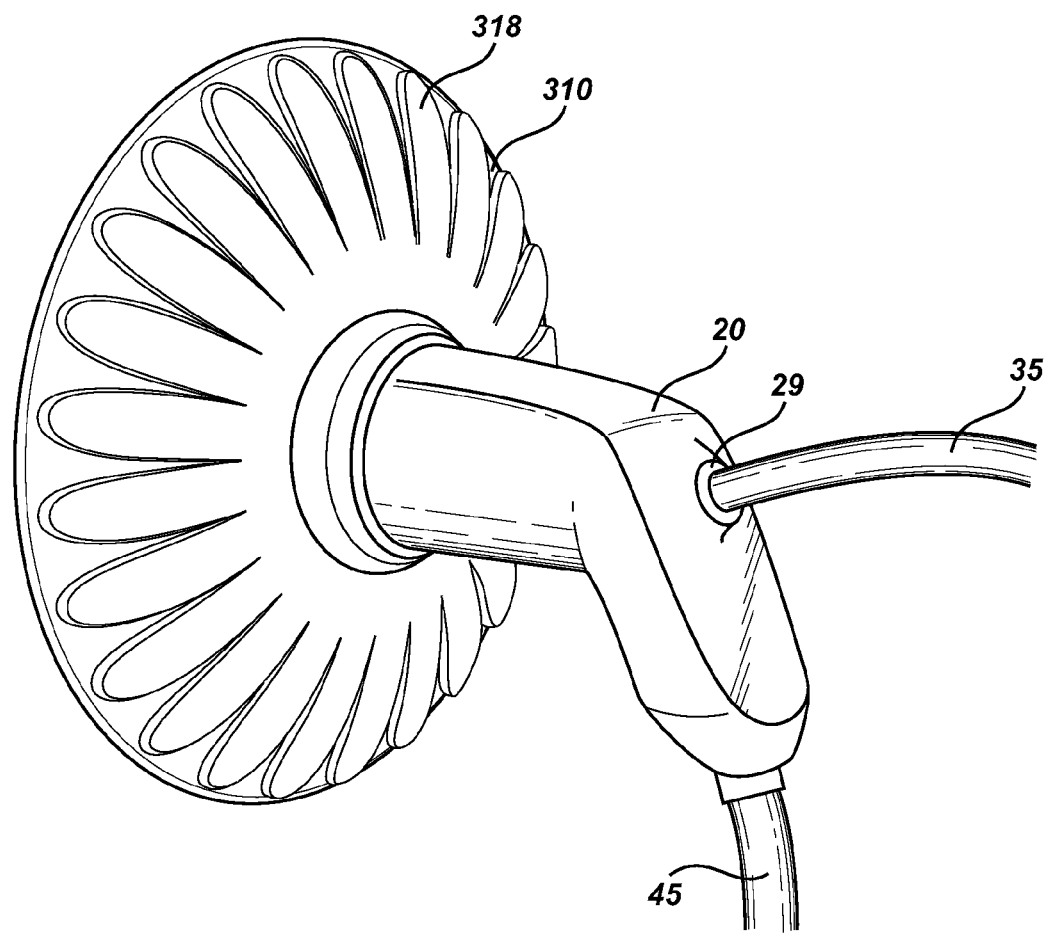
FIGS. 7 through 9 illustrate views of exemplary breast shields of exemplary embodiments of a breast pump system.
Figure 8:
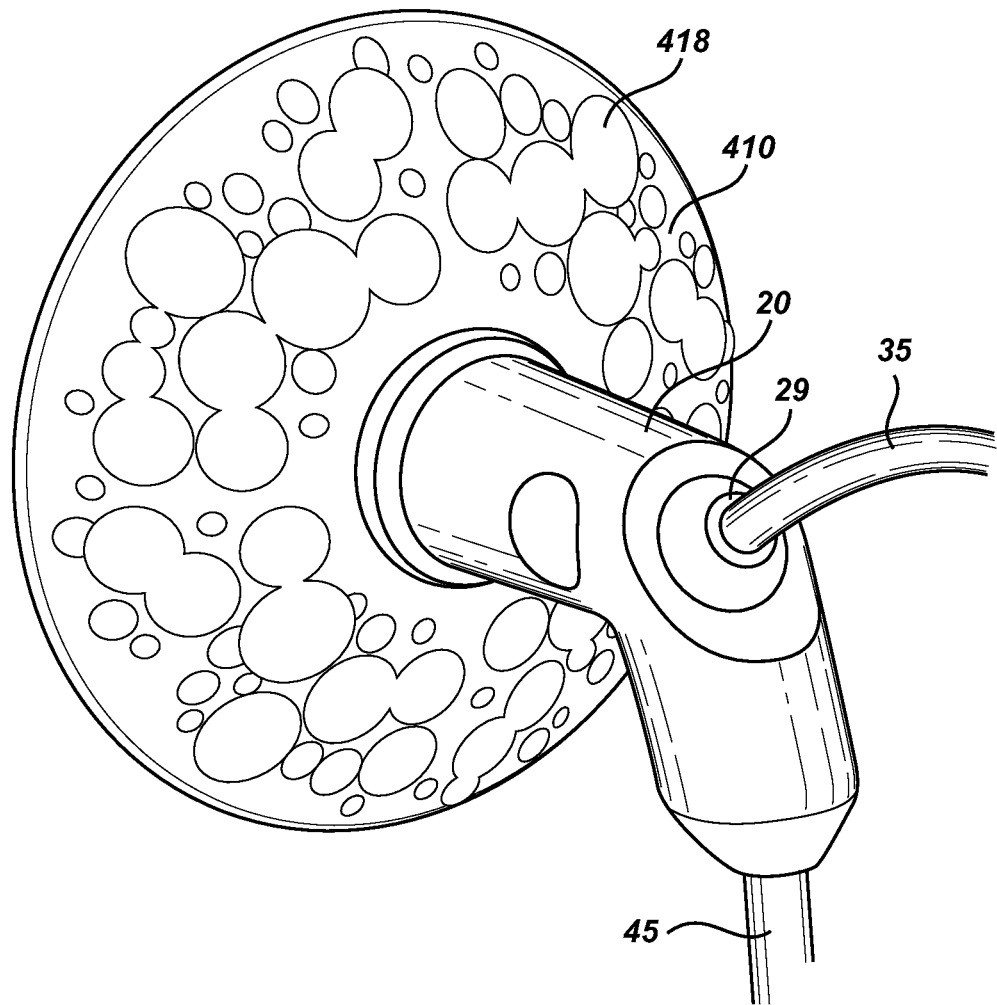
Figure 9:
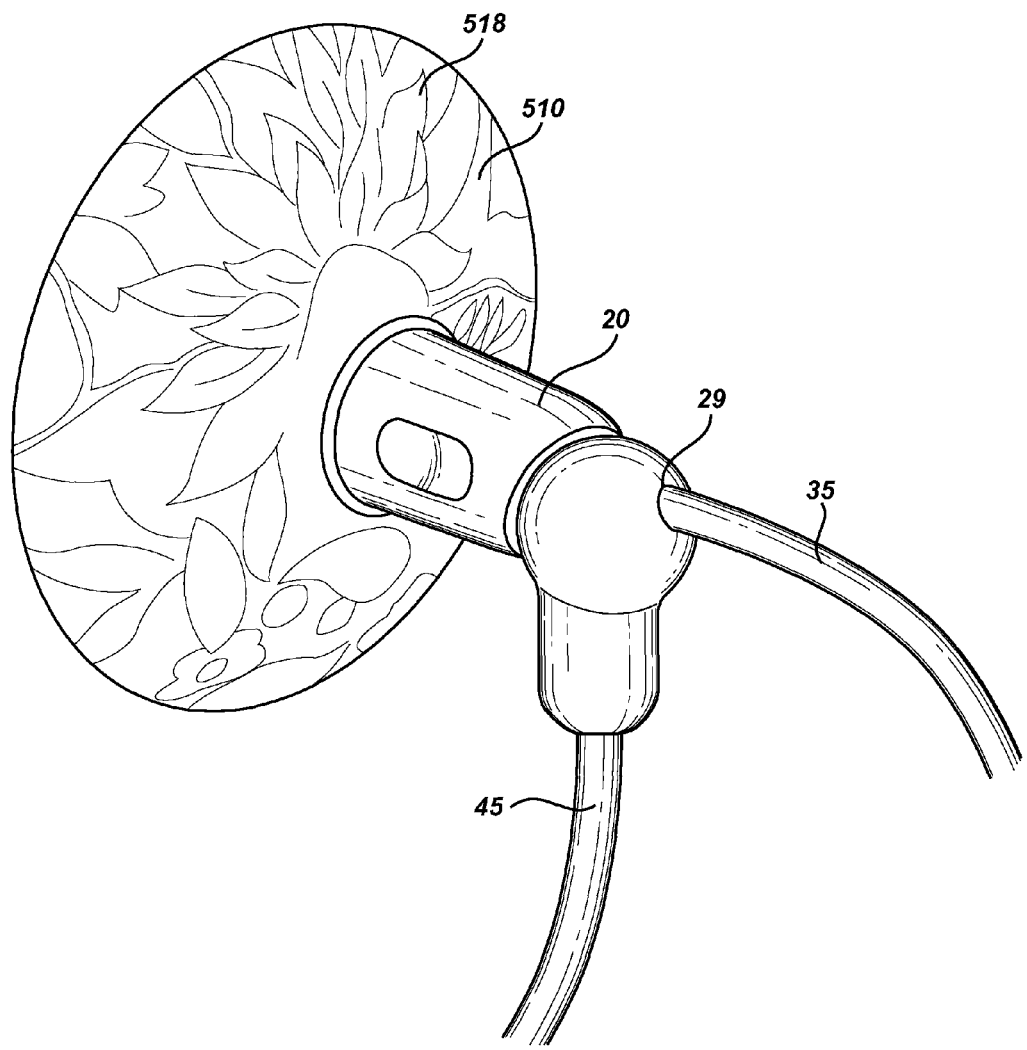

FIGS. 7 through 9 illustrate exemplary embodiments of breast shield 10 of FIGS. 1-5. Each of breast shields 310, 410, 510 includes surface features 318, 418, 518, respectively. Breast shield 310 includes surface features 318 resembling flower petals extending outwardly from adapter 20. Similarly, breast shield 410 includes surface features 418 resembling bubbles, and breast shield 510 includes surface features 518 resembling leaves or other nature-styled images. Surface features 318, 418, 518 may provide structure, and may provide additional adhesion for inner surface 14. Similarly, as shown in the Figures, adapter 20 may be provided in a number of different profiles and designs.

Figure 10:
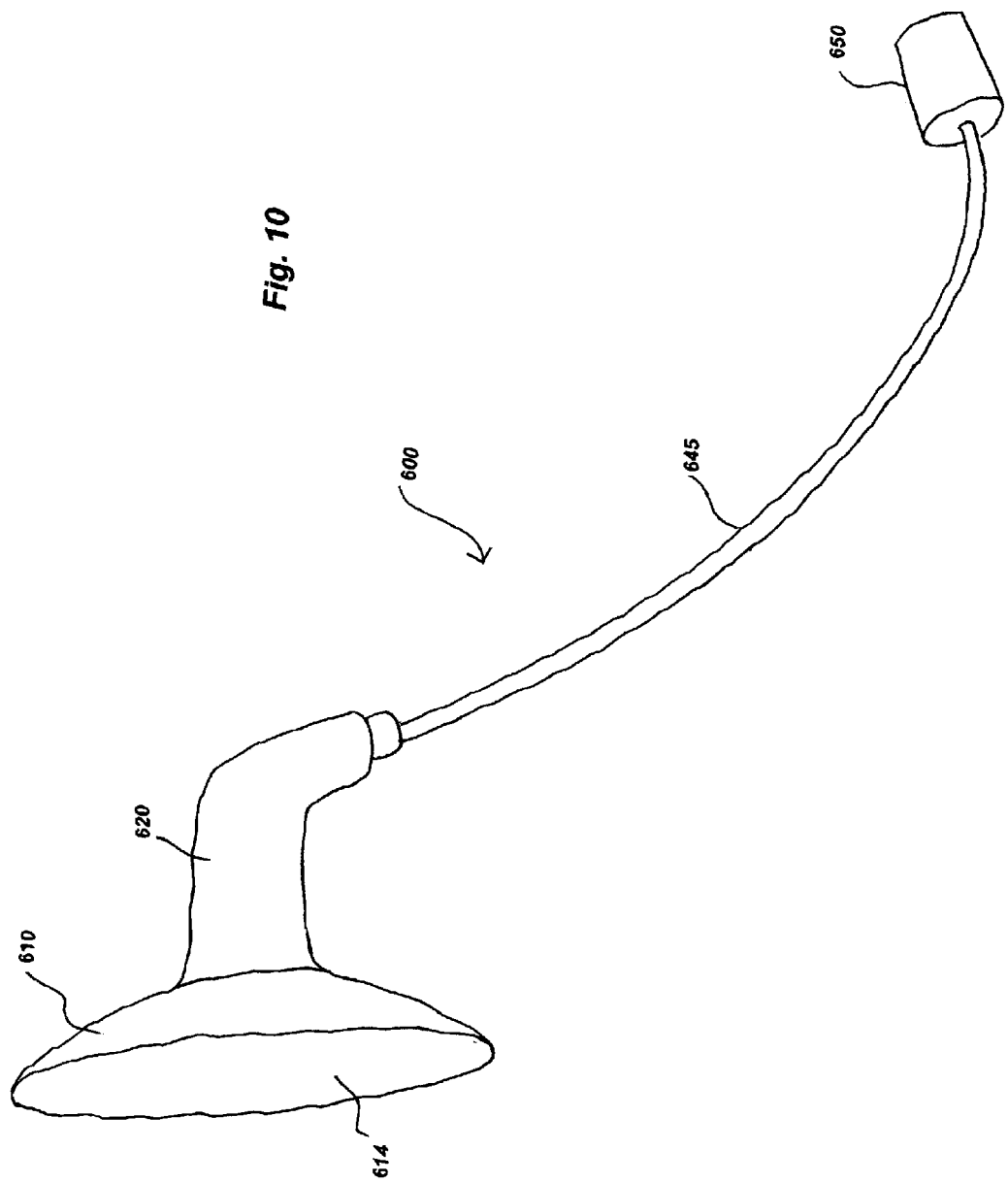
FIG. 10 illustrates a perspective view of a hands-free breast shield adapter system which can be used with a conventional breast pump system to obtain hands-free collection of breast milk without having to modify the conventional breast pump system.

While the embodiments described above provide marked advantages over conventional breast pump systems, modifications are necessary to conventional systems in order to provide the hands-free breast pumping of the invention. In some scenarios, the modifications may potentially void warrantees for the systems. In others, the user may already own and use a conventional breast pump system, but would like the hands-free benefits of the present invention at certain times. Thus, FIG. 10 shows a hands-free breast shield adapter system, generally indicated at 600. The breast shield adapter system 600 preferably includes a breast shield 610 which is designed to adhere to a woman's breast in a hands-free manner during both negative and neutral pressure cycles of pumping. This is typically accomplished by providing the breast shield 610 with an adhesive on an inner surface 614 thereof. The adhesive may cover the entire inner surface 614 or may only form a strip which is adequate to hold the breast shield 610 to a woman's breast and maintain a substantially airtight seal during the pumping process.

It is preferred that the inner surface 614 of the breast shield 610 be either formed with an adhesive material or that adhesive is applied during the manufacturing process. However, it will be appreciated that adhesive may be applied to the breast shield by the user either to initially provide adhesive qualities or to renew adhesive qualities lost by use and/or washing.

The breast shield 610 is connected to a coupling 620 which may be similar to the adapter 20 discussed above (and "coupling" as used herein includes such an adapter unless indicated to the contrary). Specifically, the coupling may be configured to be adjacent to and/or receive the nipple and extend around the areola of the woman's breast. For reasons which will be discussed below, however, the coupling 620 typically will not need to be connected directly to a vacuum line and will not need separate vacuum pressure and milk flow. Rather, the coupling 620 connects the breast shield 610 to a drain line 645 which is desired to carry milk away from the breast shield 610 and coupling 620. The drain line 645 can be used both to carry the expressed milk to the container 674, and to draw a negative pressure in the coupling 620/breast shield 610 to encourage the expression of milk.

While shown as being two separate parts, it will be appreciated that the breast shield 610 and the coupling 620 could be formed as an integral piece. Likewise, the coupling 620 and the drain line 645 could be formed as an integral piece. The breast shield 610 and coupling 620 may come in a variety of sizes to accommodate breasts having different nipple sizes.

The drain line 645 may be any desired length. However, a length of 6-24 inches is desirable, and preferably 10-18 inches as it allows the milk to be delivered to a location remote from the woman's breast. This means that the weight of the expressed milk and any collection container, such as a bottle, will not be suspended from the breast—making the system more comfortable to use and less intrusive on the woman. For example, the breast shield and adapter may be placed under the shirt and the drain line extended out of the bottom of the woman's shirt. If a person were to walk in on the woman during use, the system would be far less noticeable than having an entire pump system, such as pump system 100 hanging from the woman's breast. It has been found that a conventional pump system will work even when the container 674 which receives the expressed milk is disposed above the first breast shield 610. Thus, a woman may lay on a couch or recline in a chair if desired and the system will still collect milk in the container.

Figure 11:
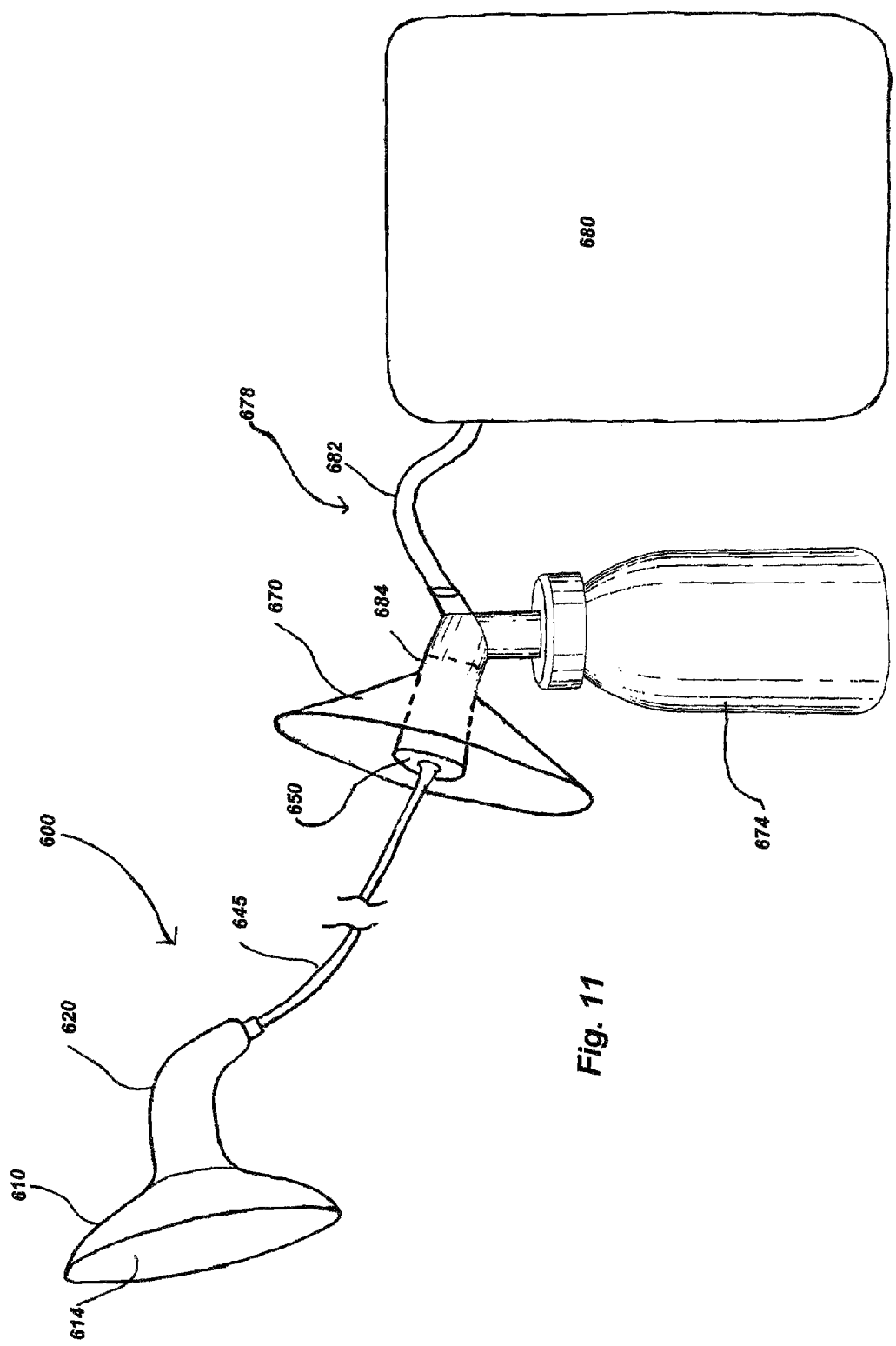
FIG. 11 illustrates the breast shield adapter system of FIG. 10 connected to a breast shield and/or adapter of a conventional breast pump system.

Disposed at or adjacent an opposing end of the drain line 645 is a connector 650. While the connector 650 could be mounted in a bottle sized with an opening comparable with the outer diameter of the connector, it is typically mounted into the opening of a breast shield 670/adapter 684 of a conventional breast pump system as shown in FIG. 11. Milk passing through the drain line 645 is passed through the connector 650 and a conventional breast shield 670 (and/or its associated adapter 684) and into a bottle 674 or other collection mechanism. From the conventional breast shield 670 on, a conventional breast pump system 678 can be used. The conventional breast pump system 678 includes the pump 680 and vacuum line 682, along with the adapter 684 which keeps the vacuum pressure and milk separate from one another during pumping. In this configuration, the drain line 645 provides both a drain for delivering milk and a communication of the negative pressure drawn through the conventional adapter 684 and/or breast shield 670 back to the breast shield 610 and coupling 620.

It will be appreciated by those of skill in the art that some breast pump systems have a breast shield which can be detached from the adaptor to accommodate different sized breast shields. In accordance with the present invention, the connector 650 can be sized to engage a plurality of breast shield sizes, and may be configured to also nest in the adapter 684 in the event that the breast shield 670 is removed.

With the breast shield adapter system 600, a woman who already owns a conventional breast pump system does not need to make any modifications to the conventional breast pump system which could affect the warranty. Likewise, she need not purchase an entire new breast pump system. When she desires to do hands-free breast pumping, she merely takes out the breast shield adapter system 600, attaches the breast shield 610 to the breast and inserts the connector 650 into the conventional breast shield 670 or adapter 684. She is then able to express milk in a hands-free manner or a one-handed manner if using a manual pump, until finished. She is also able to use the conventional breast pump system by simply removing the connector 650 from the conventional breast shield 670 if she so desires.

In addition to avoiding any modifications to existing breast pump systems which could affect warranties, the breast shield adapter system 600 reduces cost as it can rely on the vacuum/milk isolation features of the conventional breast pump system. Additionally, the same breast shield adapter system 600 can be used with multiple different existing breast pump systems. The connector 650 can be shaped so as to engage different sized breast shields, and, if necessary, can simply be replaced with a different size connector to adapt to a breast pump system with substantially different dimensions.

Figure 12:
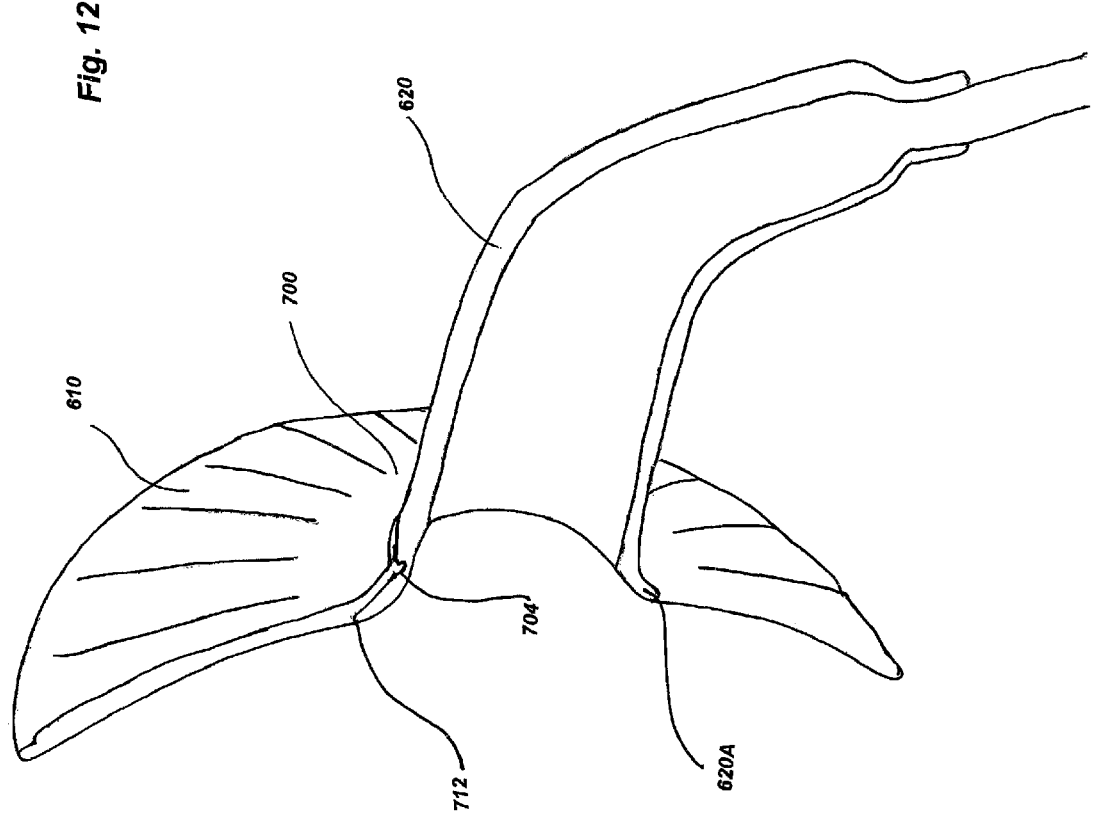
FIG. 12 shows a cross-sectional view of the breast shield and related structures of FIG. 10.

Turning now to FIG. 12, there is shown a cross-sectional view of the breast shield and related structures of FIG. 10. The breast shield 610 may engage and be held on to the coupling 620 by having an annular locating groove 700 on the coupling 620 receive an annular rib 704 on the breast shield 610. While an annular rib/groove arrangement provides a consistent and reliable attachment, it will be appreciated that neither the rib nor groove need to be annular and that other structures or attachment methods could be used to hold the breast shield 610 to the coupling 620. Also, as mentioned earlier, the two could be formed as a single structure.

It is also preferred that any interface between the proximal end 620A of the coupling and the breast shield 610 be relatively flush so as to minimize potential irritation of the areola. Thus, the breast shield 610 may include a groove 712 so that the interface is substantially flush.

The drain line 645 can be attached to the coupling 620 in a variety of ways, including being press fit, glued or welded in place. Additionally, it will be appreciated that the coupling 620 and the drain line 645 (and even the breast shield) could be formed as one integral unit.

Figure 13:
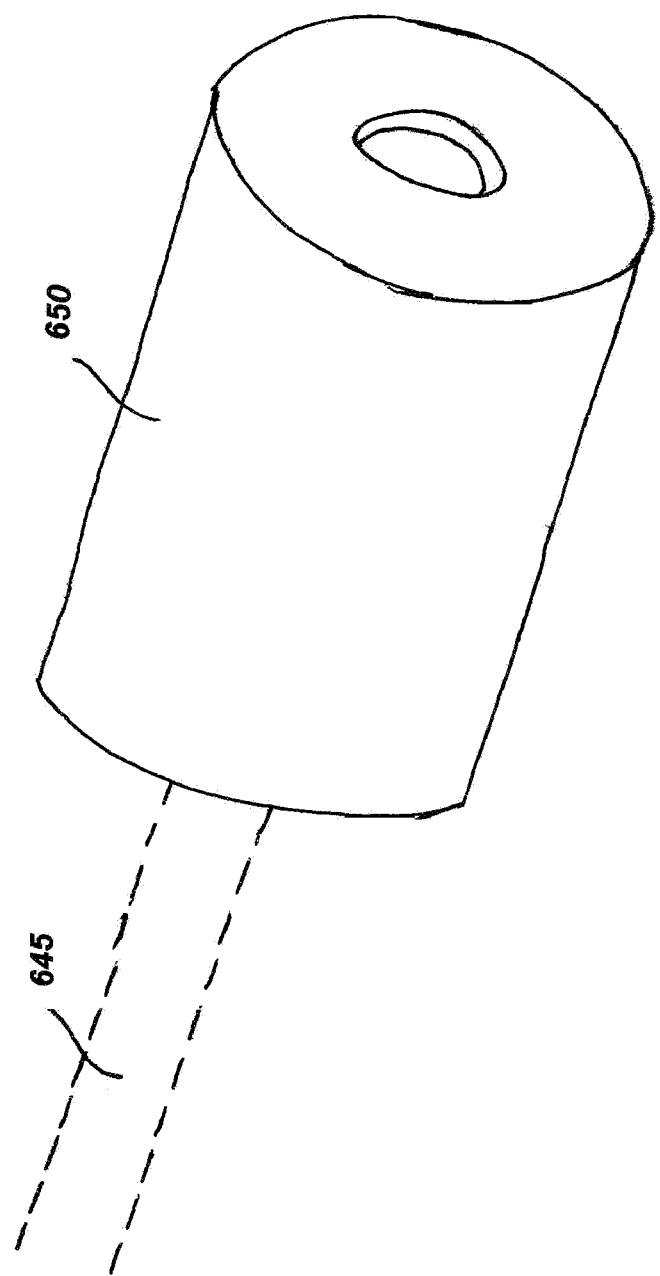
FIG. 13 shows a close-up view of a connector used for connecting the breast shield adapter system of FIG. 10 into a conventional breast shield of a conventional breast pump system.

Turning to FIG. 13, the connector 650 receives the drain line 645. The drain line 645 may extend partially into the connector 650, or may extend completely through the connector. Additionally, the drain line 645 and the connector 650 can be attached in a variety of manners (adhesives, press-fit, welding) or could be formed as an integral unit. It is preferred that the connector 650 is formed from a resilient or semi-resilient material that will engage the opening of the breast shield 670 or adapter 684 of the conventional breast pump system and form a fluid tight seal therewith.

FIG. 13 shows a close-up view of a connector 650 used for connecting the breast shield adapter system of FIG. 10 into a conventional breast shield 670 of a conventional breast pump system. The connector 650 may have a single lumen 652 extending therethrough for the drain line to extend into (or through) and for milk to pass through into the collection mechanism of the conventional breast pump system. The connector 650 is typically tapered so as to be able to connect to breast shields (or their adapters) having different sized openings.

Figure 14:
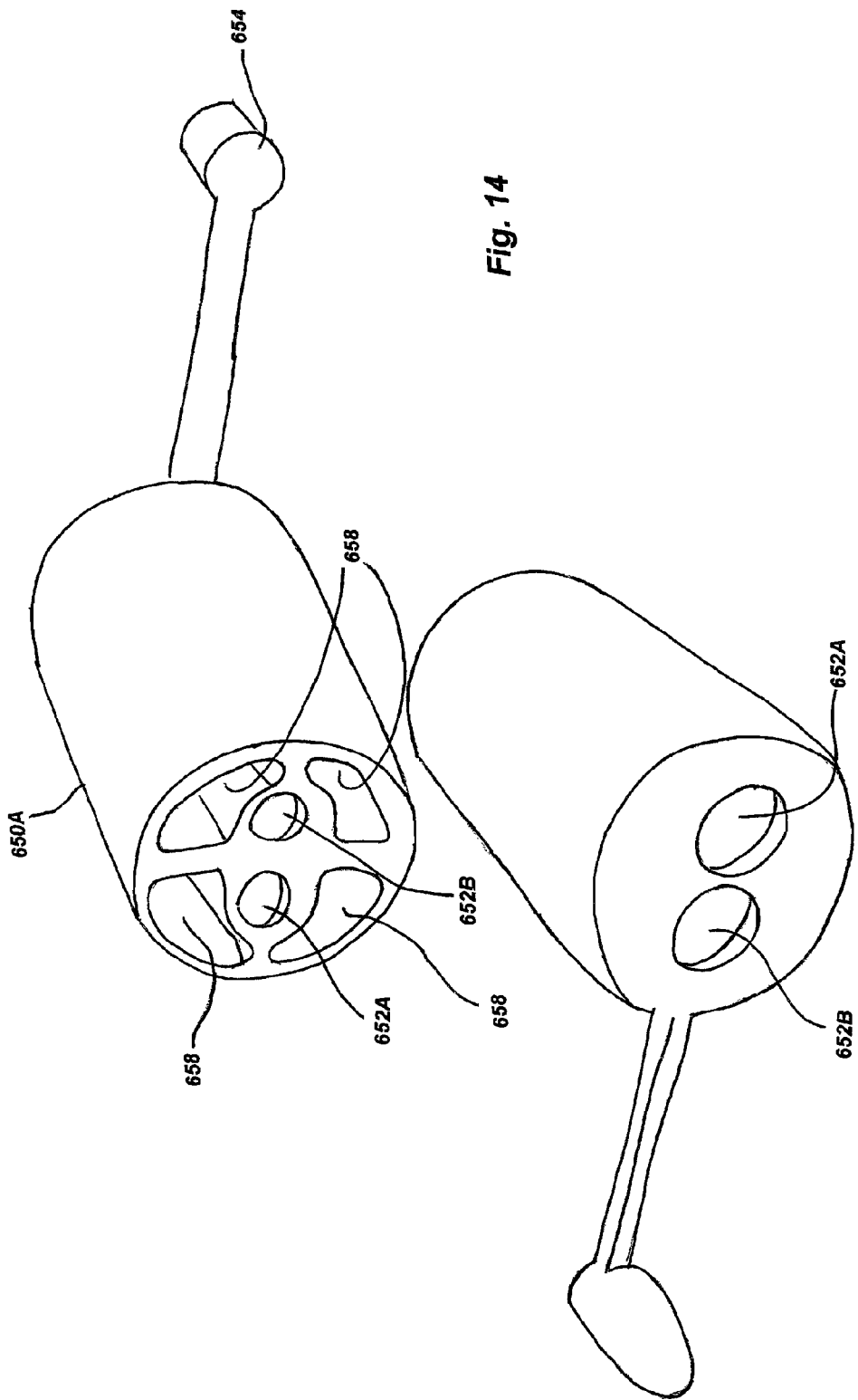
FIG. 14 shows a close-up view of an alternate embodiment of a connector.

FIG. 14 shows a close-up view of opposing ends of an alternate embodiment of a connector 650A. Rather than having a single channel, the connector 650A has two openings 652A, 652B, one of which may be closed with a plug 654. Having two channels allows two breast shields 610 to be used and drain into a single container of a conventional breast pump system. Thus, a single breast shield conventional pumping system can be used to simultaneously express milk from both breasts in a hands-free manner instead of forcing the woman to express milk from each breast in sequence and requiring the use of at least one hand to hold the conventional breast shield in place.

As shown in FIG. 14, the connector 650A may have voids 658 formed therein to reduce weight and material costs. The voids can also be used to help the connector 650A be more resilient and adaptable to breast shields having different size openings. However, it will be appreciated that a generally solid connector (other than the lumens 652A and 652B) may be used as well.

Figure 15:
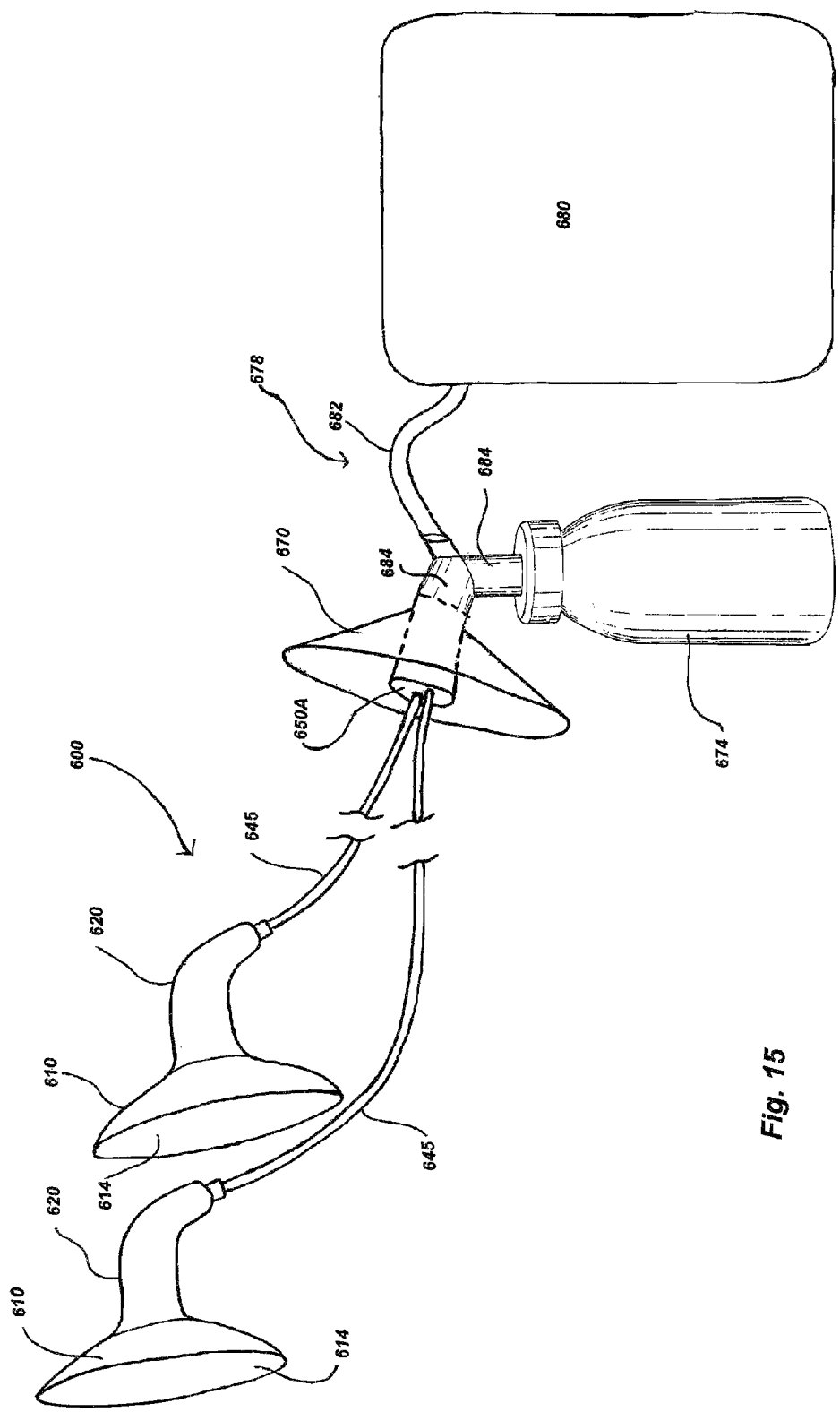
FIG. 15 shows a pair of breast shields connected to a single conventional breast shield and container in accordance with principles of the present invention.

FIG. 15 shows a pair of breast shield adapter systems 600 for use with the present invention. A pair of breast shields 610 (a first breast shield and a third breast shield) are provided with an adhesive inner surface 614. Each breast shield 610 is connected to a coupling 620 and drain line 645 as discussed above. The two drain lines 645 may be attached to a single adapter 650A for mounting in a conventional breast shield 670 (a second breast shield) or an adapter 684 to which the second breast shield would normally be attached in a conventional pump system 678. If the conventional system lacks sufficient power to extract the milk, one of the drain lines 645 can be withdrawn from the connector 650A and the plug 654 (FIG. 14) can be used to close one of the channels or lumens 652A or 652B. The removed drain line 645 can then be attached to another connector 650/650A and attached to another pump system 678 so that milk can be expressed from both breasts simultaneously. This allows a woman to work with both hands and to minimize the disruption to her day caused by the need to pump breast milk.

Some commercially available pumps provide two pump lines so that a woman can use two breast shields to express milk into associated containers at the same time. If use with only one breast shield is desired, one pump line can be removed and the vacuum line opening plugged. One advantage of the configuration shown in FIG. 15 is that a woman using the system needs to only deal with one container 674 for collecting milk. For example, when used in an office setting, the container 674 may be held between the woman's legs while she works. A single container 674 is easier to use and it is less likely that the container will slip off the chair during use. However, if the suction is inadequate, the connector 650A can be quickly reconfigured and one of the breast shields 610, couplings 620 and drain lines 645 can be attached to another connector (such as 650 in FIG. 13) and then attached to a conventional breast shield 670 or adapter 684 so that milk from the two breasts are expressed into separate containers. Thus, a user may quickly adapt the system to a configuration which is most convenient.

It should be understood that the disclosed embodiments of the breast pump systems and adapter systems are exemplary only and do not limit the breadth of the disclosure. Likewise, it should be understood that the shape, material, edge design, and surface area of the illustrated embodiments are only exemplary of embodiments of breast shields and are not limiting, as breast shields falling within the scope of the appended claims may have different shapes, edge profiles, etc., while performing the same function.

As will be apparent to those skilled in the art in which the invention is addressed, the present invention may be embodied in forms other than those specifically disclosed above without departing from the spirit or potential characteristics of the invention. Particular embodiments of the present invention described above are therefore to be considered in all respects as illustrative and not restrictive. The scope of the present invention is as set forth in the appended claims and equivalents thereof rather than being limited to the example contained in the foregoing description.

What is claimed is:

1. A method for expressing milk from a breast, the method comprising:
   adhesively attaching to a woman's breast a first breast shield having an adhesive inner surface and an opening connected to a first end of an elongate flexible tube, wherein a second end of the elongate flexible tube is connected to a connector configured to be fluidly connected within an opening of a second breast shield of a conventional breast pump system having a milk container, wherein the breast pump system and milk container is not suspended from or supported by the woman's breast;
   inserting the connector within the opening of the second breast shield of the breast pump system;
   applying suction through the opening of the first breast shield to express milk from the breast and conducting the milk from the first breast shield through the elongate flexible tube and connector to the opening of the second breast shield of the breast pump system and into the milk container; and
   collecting the milk in a container for later use.

2. The method according to claim 1, wherein the method comprises using an elongate tube which is at least 10 inches long.

* * * * *